United States Patent
Fatemi

(10) Patent No.: US 10,252,186 B2
(45) Date of Patent: Apr. 9, 2019

(54) AUTOMATED SOLID PHASE EXTRACTION

(71) Applicant: Zist Abzar Pajoohan, Tehran OT (IR)

(72) Inventor: Seyed Kamal Fatemi, Tehran (IR)

(73) Assignee: ZIST ABZAR PAJOOHAN, Tehran (IR)

(*) Notice: Subject to any disclaimer, the term of this patent is extended or adjusted under 35 U.S.C. 154(b) by 234 days.

(21) Appl. No.: 15/232,313

(22) Filed: Aug. 9, 2016

(65) Prior Publication Data

US 2016/0346712 A1    Dec. 1, 2016

(51) Int. Cl.

| | |
|---|---|
| *B01D 15/14* | (2006.01) |
| *B01D 15/20* | (2006.01) |
| *B01D 15/42* | (2006.01) |
| *G01N 1/40* | (2006.01) |
| *G01N 35/00* | (2006.01) |
| *G01N 35/10* | (2006.01) |
| *G01N 30/00* | (2006.01) |
| *G01N 35/04* | (2006.01) |

(52) U.S. Cl.
CPC .......... *B01D 15/424* (2013.01); *B01D 15/14* (2013.01); *B01D 15/20* (2013.01); *B01D 15/203* (2013.01); *B01D 15/42* (2013.01); *G01N 1/40* (2013.01); *G01N 1/405* (2013.01); *G01N 35/00* (2013.01); *G01N 35/10* (2013.01); *G01N 35/1002* (2013.01); *G01N 2001/4027* (2013.01); *G01N 2030/009* (2013.01); *G01N 2035/00801* (2013.01); *G01N 2035/0484* (2013.01)

(58) Field of Classification Search
CPC ...... B01D 15/14; B01D 15/20; B01D 15/203; B01D 15/42; B01D 15/424; G01N 1/40; G01N 1/405; G01N 35/00; G01N 35/10; G01N 35/1002; G01N 2001/4027; G01N 2030/009; G01N 2035/00801; G01N 2035/0484

See application file for complete search history.

(56) References Cited

U.S. PATENT DOCUMENTS

| | | | | |
|---|---|---|---|---|
| 5,260,028 A | * | 11/1993 | Astle ................. | G01N 1/405 210/635 |
| 5,660,792 A | * | 8/1997 | Koike ................. | G01N 35/00 422/536 |
| 6,133,045 A | * | 10/2000 | Johnson ............. | B01L 3/50255 210/406 |

(Continued)

OTHER PUBLICATIONS

Oliver Lerc, Comprehensive automation of the solid phase extraction gas chromatographic mass spectrometric analysis (SPE-GC/MS) of opioids, cocaine, and metabolites from serum and other matrices, Anal Bioanal Chem., Jul. 2014, vol. 416, Issue 18, pp. 4443-4451.

(Continued)

*Primary Examiner* — Katherine Zalasky
*Assistant Examiner* — Benjamin L Lebron
(74) *Attorney, Agent, or Firm* — NovoTechIP International PLLC

(57) ABSTRACT

In a solid phase extraction (SPE) apparatus, a cartridge housing tray houses a plurality of SPE cartridges. A liquid loading assembly applies liquid samples and SPE solutions into the plurality of cartridges. A liquid drawing assembly forces the liquid samples and the SPE solutions once they are applied to pass through the plurality of the SPE cartridges.

9 Claims, 14 Drawing Sheets

(56) References Cited

U.S. PATENT DOCUMENTS

2004/0013572 A1    1/2004  Moore

OTHER PUBLICATIONS

R.J. Lewis, Simultaneous analysis of Thebaine, 6-MAM and six abused opiates in postmortem fluids and tissues using Zymark® automated solid-phase extraction and gas chromatography—mass spectrometry, Journal of Chromatography B, Aug. 5, 2005, vol. 822, Issues 1-2, pp. 137-145.
Marie Kjargaard Bjork, Determination of 19 drugs of abuse and metabolites in whole blood by high-performance liquid chromatography—tandem mass spectrometry, Anal Bioanal Chem., Apr. 2010, vol. 396, pp. 2393-2401.

* cited by examiner

AUTOMATED SOLID PHASE EXTRACTION

TECHNICAL FIELD

The present application generally relates to solid phase extraction, particularly, to systems and methods of solid phase extraction.

BACKGROUND

Solid phase extraction (SPE) is a sample preparation method that can include individual steps of: first, conditioning a sorbent material; second, application of a sample to the sorbent material; third, rinsing and cleaning the applied sample; and finally desorption and recovery of analytes to be separated. Work sequences can include repeated, time-consuming operations such as packing of sorbent materials in cartridges, introducing and drawing liquid samples and solutions (e.g., activating solvents, washing buffers and eluting solvents) into and out of the SPE cartridges.

SUMMARY

The following brief summary is not intended to include all features and aspects of the present application, nor does it imply that practices must include all features and aspects discussed in this summary.

Various exemplary apparatuses are disclosed, and examples can include an apparatus for solid phase extraction (SPE), and implementations of the apparatus can include a cartridge housing tray configured to house a plurality of SPE cartridges, each of the SPE cartridges having an inlet and an outlet; and can include a liquid loading assembly. Example implementations of the liquid loading assembly can be configured, for example, to: introduce a respective amount of an activating solvent into the inlet of each of the SPE cartridges, transfer into the respective inlets of the plurality of SPE cartridges a corresponding plurality of samples, each to a corresponding one of the inlets, and introduce a respective amount of a washing solution into the inlet of each of the SPE cartridges, and introduce a respective amount of an eluting solvent to the inlet of each of the SPE cartridges. One example implementation of the apparatus can also include a liquid drawing assembly, configured to selectively apply a drawing driving force to the outlets of the SPE cartridges to draw out of all the SPE cartridges, from their respective outlets and into a pan, the respective activating solvent and washing solution introduced into the inlets by the liquid loading assembly, and to draw eluting solvent out of all the SPE cartridges, through their respective outlets, and to collect the drawn eluting solvent in a corresponding plurality of eluate containers. In an aspect, the liquid drawing assembly can be configured to evaporate the eluting solvent from the plurality of eluate containers.

In one example implementation, the inlet can be an upper inlet, at an upper end of the SPE cartridge, and the outlet can be a lower outlet, at a lower end of the SPE cartridge. In a further example implementation the liquid drawing assembly can include a vacuum chamber connected to the lower outlets of the plurality of the SPE cartridges, and can include an eluate container movable support, configured to support and move the plurality of the eluate containers, along a horizontal axis, to an eluate loading position and away from the eluate loading position. In an aspect, the vacuum chamber can be configured to apply a vacuum at the lower outlet of the plurality of the SPE cartridges as the drawing driving force. In another aspect, in the eluate loading position, each of the plurality of eluate containers can be under the lower outlet of a respective one of the SPE cartridges, to collect the respective eluate drawn from the lower outlet.

In one example implementation, the vacuum chamber can be further configured to apply a vacuum at the lower outlet of the plurality of the SPE cartridges to force the samples transferred into the respective inlets of the plurality of SPE cartridges downward inside the SPE cartridges.

In one example implementation, the eluate container movable support can include tray guide bars, extending along the horizontal axis, a movable eluate container tray configured to support the plurality of eluate containers and movably coupled to the tray guide bars, and a tray moving mechanism coupled to the movable eluate container tray. In an aspect, the movable eluate container tray can be movably coupled to the tray guide bars in a configuration wherein the movable eluate container tray is constrained by the tray guide bars to movement along the horizontal axis.

In one example implementation, the movable eluate container tray can include a heating mechanism configured to evaporate, within the vacuum of the vacuum chamber, the eluting solvent from the eluate in the eluate containers.

In one implementation, the apparatus can further include a sample tray, configured to hold a plurality of sample containers, and the liquid loading assembly can include a frame guide, extending along a vertical axis, the vertical axis being normal to the horizontal axis, and a movable frame, movably coupled to the frame guide, in a configuration constraining the movable frame to a vertical movement, parallel to the vertical axis, between positions that include a loading position and a preloading position. One example liquid loading assembly can further include a linear actuating mechanism, coupled to the movable frame and configured to selectively urge the vertical movement, and can include a plurality of probe assembles, supported by the movable frame, each of the probe assemblies corresponding to one of the sample containers, and each of the probe assemblies including a suction probe and a sample outlet. One example liquid loading assembly can also include a sample pump, connected to the plurality of sample outlets by a corresponding plurality of tubes, and a plurality of injector lines, each connected at one end to an output of the sample pump and each having a distal end. In one example implementation, the plurality of probe assembles and the movable frame can be configured such that, in the loading position, the suction probe goes into the corresponding sample container and, in the loading position, the sample pump can draw a respective content of each of the sample containers through a corresponding one of the tubes, and injects the content through a corresponding one of the injector lines into the upper inlet of a corresponding one of the SPE cartridges.

In one disclosed implementation, the liquid loading assembly can further include a shaft, extending along a longitudinal axis, supported to be rotatable about the longitudinal axis, a plurality of tube holders, each mounted on the shaft, each supporting the distal end of a corresponding one of the injector lines, and a motor, coupled to the shaft, wherein a rotation of the motor can drive a roll rotation of the shaft about the longitudinal axis, between a horizontal loading position and a vertical idle position. In one example implementation, in the horizontal loading position, while the movable frame is in the loading position, the distal end of each the plurality of injector lines can be proximal to the upper inlet of a corresponding one of the SPE cartridges.

In one disclosed implementation, the cartridge housing tray can be configured to house the plurality of SPE cartridges in an arrangement where the respective upper inlets are aligned linearly along an alignment axis that extends perpendicular to the horizontal axis and normal to the vertical axis. In one disclosed implementation, the apparatus can further include a movable loading member, selectively movable in a direction parallel to the alignment axis, to respective positions, each of the positions being above the upper inlet of a corresponding one of the SPE cartridges and, at each of the positions, to selectively introduce the respective amount of activating solvent through the upper inlet into the SPE cartridge.

In one disclosed example implementation, the movable loading member can include a solution inlet and a solution outlet, wherein the apparatus can further include a side pump, the side pump being configured to selectively pump the respective amount of activating solvent from an activating solvent container, into the solution inlet, and out from the solution outlet into the inlet of the SPE cartridge.

In one disclosed example implementation, the side pump can be configured to selectively pump the respective amount of washing solution, from a washing solution container, into the solution inlet, and out from the solution outlet into the inlet of the SPE cartridge.

In one disclosed example implementation, the side pump can be configured to selectively pump the respective amount eluate solvent, from an eluate solvent container, into the solution inlet, and out from the solution outlet into the inlet of the SPE cartridge.

Example methods are disclosed, including one method for solid phase extraction (SPE), including operations of providing a plurality of SPE cartridges, each of the SPE cartridges having an inlet and an outlet, introducing an amount of SPE solution activating solvent into the inlet of each of the SPE cartridges, concurrently drawing from the respective outlets of the SPE cartridges, and into a pan, the SPE solution activating solvent introduced into the respective inlets, transferring into the respective inlets of the plurality of SPE cartridges a corresponding plurality of samples, each to a corresponding one of the inlets, introducing a respective amount washing solution into the inlet of each of the SPE cartridges, concurrently drawing from the respective outlets of the SPE cartridges, and into the pan, the washing solution introduced into the respective inlets, introducing a respective amount of eluting solvent to the inlet each of the SPE cartridges, drawing the eluting solvent out of all the SPE cartridges, from their respective outlets, and collecting the respective drawn eluate in a corresponding plurality of eluate containers, and evaporating the eluting solvent from the plurality of eluate containers.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. Practices according to concepts disclosed by the present application are not intended to be limited to the implementations shown, are to be accorded the widest possible scope consistent with the principles and features disclosed herein.

A system and apparatus for automatic implementation of SPE method are described in the present disclosure. Disclosed systems and methods directed to automatic implementation of SPE method can include an automated SPE apparatus comprising a liquid loading assembly, a cartridge housing tray, and a liquid drawing assembly. The liquid loading assembly, in an aspect, can be configured to introduce liquid samples, and SPE solutions including activating solvents, washing buffers, and eluting solvents (i.e., eluents) into a plurality of SPE cartridges housed in the cartridge housing tray. The liquid drawing assembly can be configured to force the liquid samples and SPE solutions to pass through the plurality of SPE cartridges using a driving force (i.e., drawing driving force), for example, either vacuum or positive pressure. In an aspect, the liquid drawing assembly can be further configured to collect the eluate discharged from the plurality of the SPE cartridges and concentrate the components of interest in the eluate via evaporating the eluent form the eluate solution. Benefits of these features can include, but are not limited to, handling a larger amount of liquid samples, and avoiding human errors. Further benefit of the fully automated implementation of an SPE method using the automated SPE apparatus of the present disclosure can include, but is not limited to, lower human exposure to toxic materials used in an SPE process.

Figure 1:
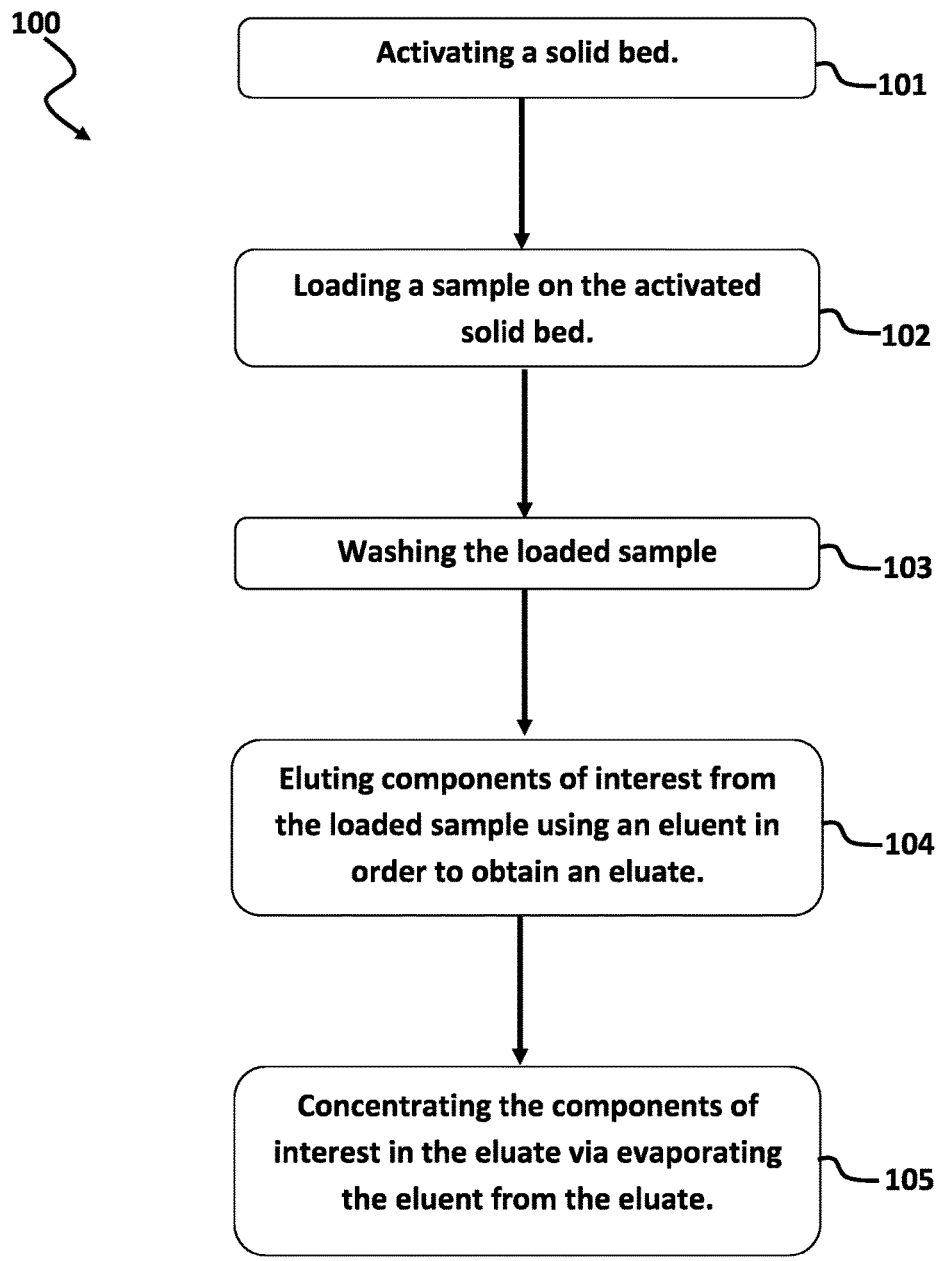
FIG. 1 is a flowchart of an example of an SPE process.

Referring to FIG. 1, example operations in one SPE method 100 can include: activating a solid bed that is formed by a sorbent material (step 101); loading a sample on the activated solid bed (step 102); washing the loaded sample (step 103); eluting a compound of interest from the loaded sample using an eluent in order to obtain an eluate (step 104); and concentrating the compound of interest in the eluate via evaporating the eluent from the eluate (step 105).

Referring to step 101, activating a solid bed (i.e., stationary or bonded phase) can include wetting the solid bed with a solvent to make the sorbent material compatible with the sample solution to ensure consistent interaction between the components of interest in the sample (i.e., analytes) and the sorbent material. In reversed-phase SPE, the sorbents can be activated by, for example, a water miscible solvent, such as methanol, isopropanol, acetonitrile, etc. In normal-phase SPE, the sorbents can be activated by, for example, solvents with low polarity, such as hexane, toluene, etc. The activation can be followed by an equilibration that can be carried out via wetting the sorbent by water or a buffer solution.

Moving on to step 102, loading the sample on the activated bed can include introducing (i.e., applying) the sample into the solid bed with a consistent flow rate to ensure an optimal retention of the sample in the solid bed. As used herein, "an optimal retention of the sample in the solid bed" means "formation of a thin liquid film of the sample over a large surface area of the sorbent material in the solid bed". In an aspect, introducing the sample into the solid bed can include slowly passing the sample through the solid bed, using either vacuum or positive pressure as the drawing driving force.

Moving on to step 103, washing the loaded sample can include using a washing solution or buffer to remove interferences that are co-retained with compounds of interest during sample loading (step 102). In other words, as used herein, "interferences" are compounds that are retained in the sorbent material of the solid bed along with the compounds of interest. For interference laden samples, for example, biological fluids (e.g., serum, plasma, urine, etc.), a washing step may be necessary to elute interferences without prematurely eluting compounds of interest.

Moving on to step 104, eluting a compound of interest from the loaded sample can include passing a solution of a solvent or a mixture of solvents that are immiscible in the original liquid sample through the wetted sorbent material. As the solvent or the mixture of solvents (i.e., eluent or eluting solvent) passes through the wetted sorbent material, the eluent can come in contact with the thin liquid film of the sample that is spread over the large surface area of the sorbent material. Once intimate contact between the sample and the eluent is achieved, the compound of interest can be extracted from the sample by the eluent. The resultant solution (i.e., eluate) that emerges from the solid bed can include both the compound of interest and the eluent.

Moving on to the final step 105, concentrating the compound of interest in the eluate (i.e., eluate concentration) can include evaporating the eluent from the eluate solution to obtain the compound of interest concentrated enough for detection by methods (e.g., liquid chromatography, gas chromatography, etc.) that can follow the SPE process.

Figure 2:
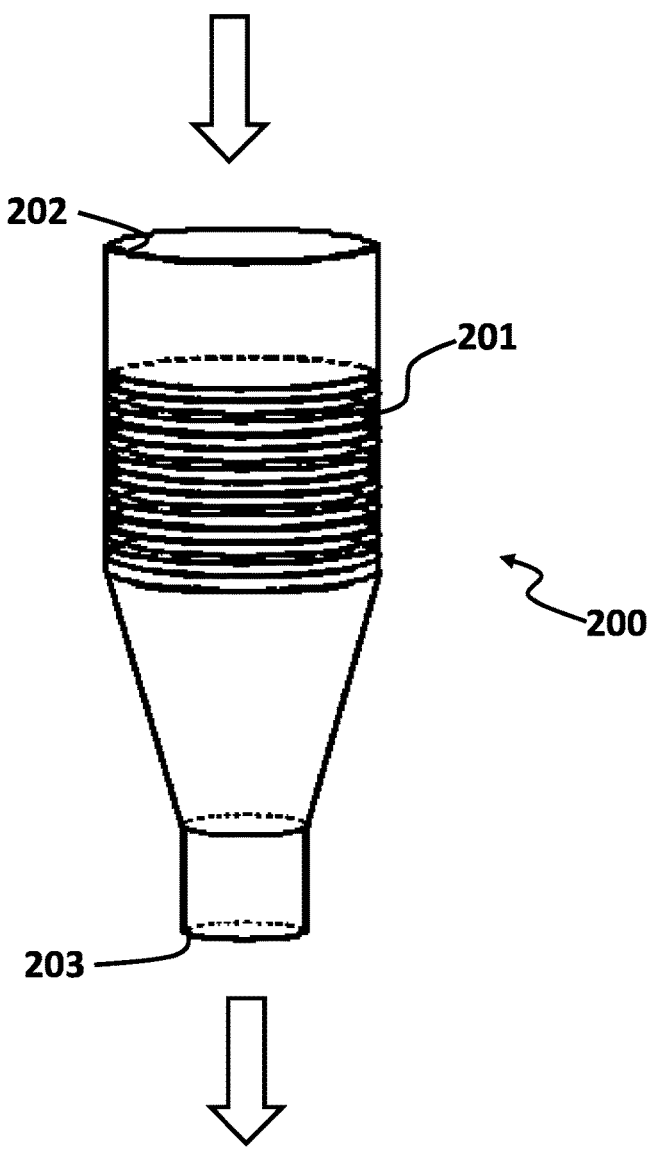
FIG. 2 illustrates an example SPE cartridge, according to one or more aspects of the present application.

Referring to FIG. 2, an example SPE cartridge 200 can include a solid bed 201, an upper inlet 202 for introducing liquids into the SPE cartridge 200 and a lower outlet 203 for liquid discharge from the SPE cartridge 200. The lower outlet 203 can be configured, for example, as a nozzle. The liquid sample and the SPE solutions (i.e., activating solvent, washing solution or buffer, and the eluent) can be introduced into the SPE cartridge 200 via the upper inlet 202, and the eluate can be drawn from the SPE cartridge 200 through the lower outlet 203.

Figure 3:
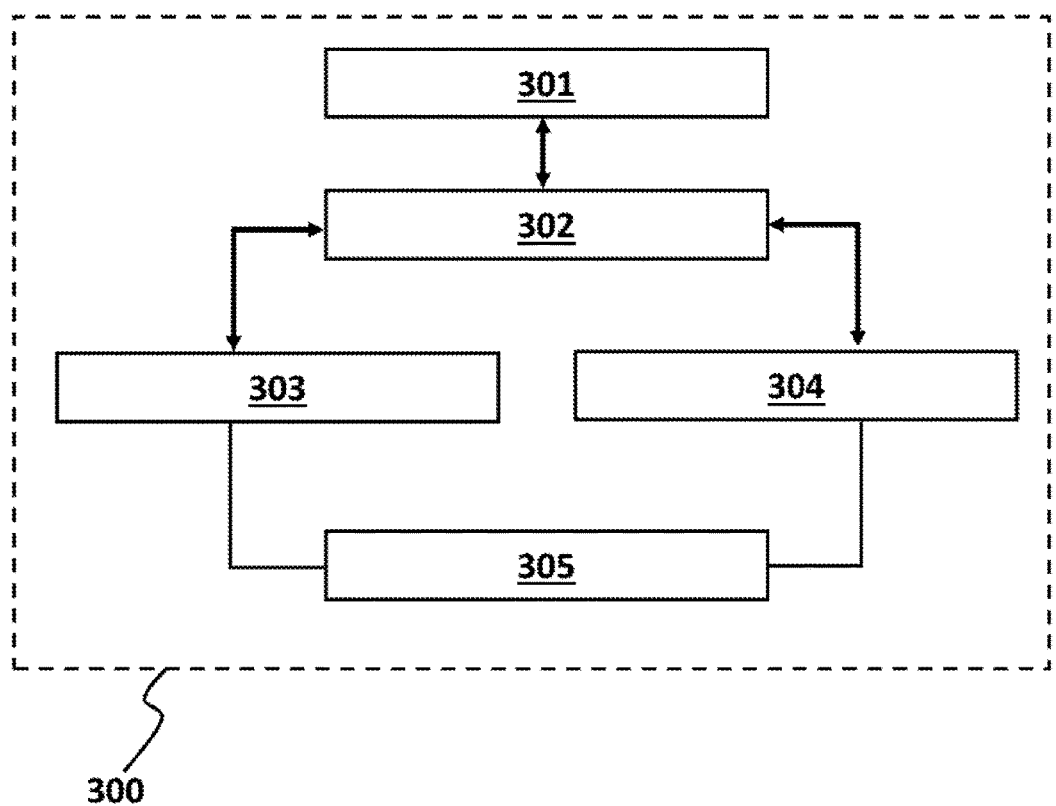
FIG. 3 illustrates a schematic block diagram of one example implementation of an automatic SPE system, according to one or more aspects of the present application.

FIG. 3 is a schematic functional block diagram of one implementation of an example automatic SPE system 300 according to one or more aspects of this disclosure. The automatic SPE system 300 can include a user interface unit 301, a controller 302, a liquid loading assembly 303, a liquid drawing assembly 304, and a cartridge housing tray 305. The cartridge housing tray 305 can be configured to house a plurality of SPE cartridges (such as the SPE cartridges 200, not explicitly visible in FIG. 3).

The liquid loading assembly 303 can be configured, as will be described in greater detail in subsequent sections of this disclosure, to introduce SPE solutions and liquid samples into the plurality of SPE cartridges housed in the cartridge housing tray 305 in the order described in connection with FIG. 1 SPE method 100.

The liquid drawing assembly 304 can be configured, as will also be described in greater detail in subsequent sections, to force the liquid samples and the SPE solutions to pass through the plurality of SPE cartridges using a drawing driving force, for example, either vacuum or positive pressure. In an aspect, the liquid drawing assembly 304 can be further configured to collect the eluate discharged from the plurality of the SPE cartridges and concentrate the components of interest in the eluate via evaporating the eluent from the eluate solution.

The controller 302 can be coupled to the liquid loading assembly 303, the liquid drawing assembly 304, and the user interface unit 301 through, for example, wired links (not explicitly visible in FIG. 3), wireless links (not explicitly visible in FIG. 3), or a combination of wired and wireless links. The controller 102 can be configured to control the operations of the liquid loading assembly 303, and the liquid drawing assembly 304.

The controller 302 can be configured with a memory (not explicitly visible in FIG. 3) for including executable instructions such that, upon execution, the liquid loading assembly 303 and the liquid drawing assembly 304 can be controlled in performing operations to further processes and methods disclosed herein. Such operations can include, for example: first, introducing an activating solvent into the plurality of SPE cartridges housed in the cartridge housing tray 305 and forcing the activating solvent to pass through the SPE cartridges by either vacuum or positive pressure; second, introducing a liquid sample containing a compound of interest into the plurality of SPE cartridges housed in the cartridge housing tray 305 and forcing the liquid sample to be loaded in the SPE cartridges using either vacuum or positive pressure; third, washing the loaded sample to elute the interferences; fourth, drying the plurality of SPE cartridges via forcing air to pass through the cartridges using either vacuum or positive pressure; fifth, introducing an eluting solvent (i.e., eluent) into the plurality of SPE cartridges housed in the cartridge housing tray 305 and forcing the eluent to pass through the SPE cartridges by either vacuum or positive pressure in order to separate the compound of interest from the loaded sample into an eluate solution; and finally evaporating the eluent from the eluate solution in order to concentrate the separated compound of interest.

The user interface unit 301 can provide means for receiving data input from a user and can function as an indicator of different sensor read-outs. One example implementation of the user interface unit 301 can include, for example, a graphical user interface (GUI) unit.

Figure 4A:
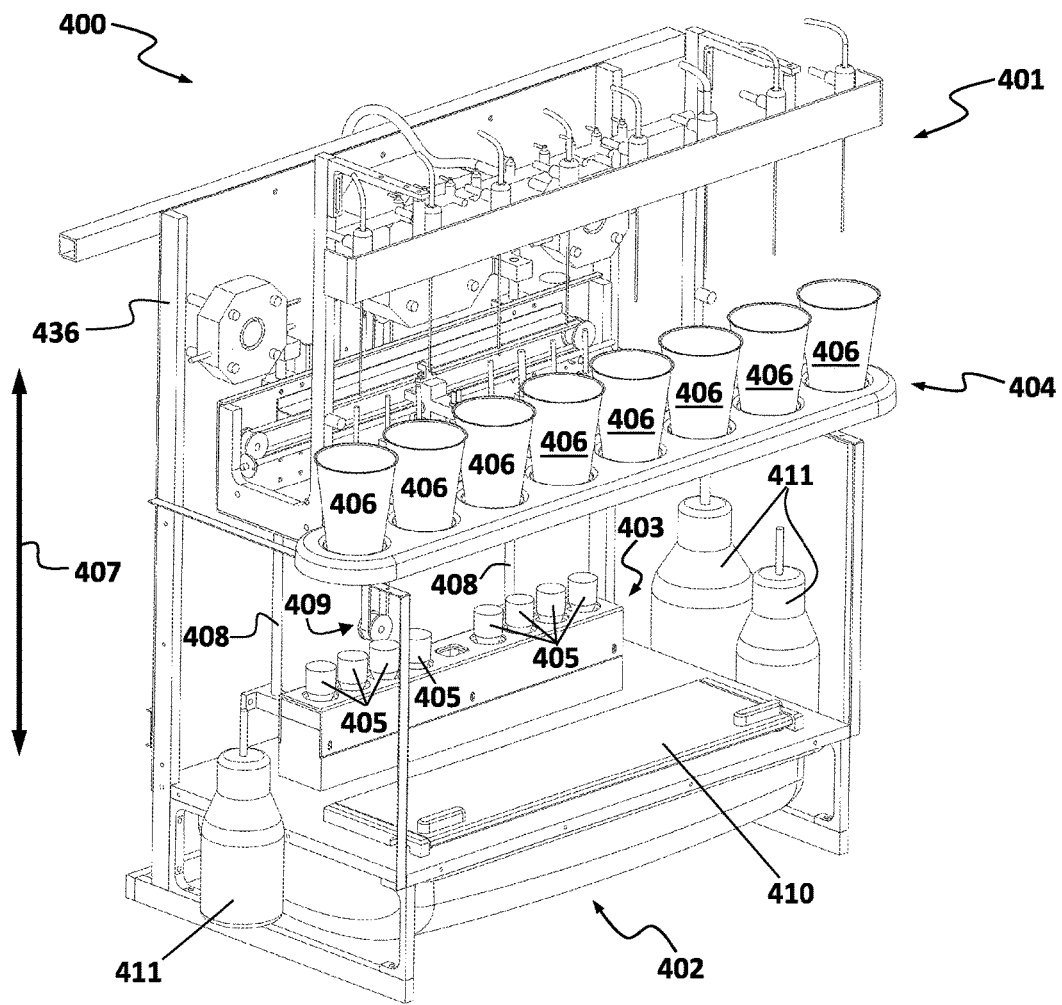
FIG. 4A illustrates a perspective view of one example automatic SPE apparatus in a pre-loading position, according to one or more aspects of the present application.
Figure 4B:
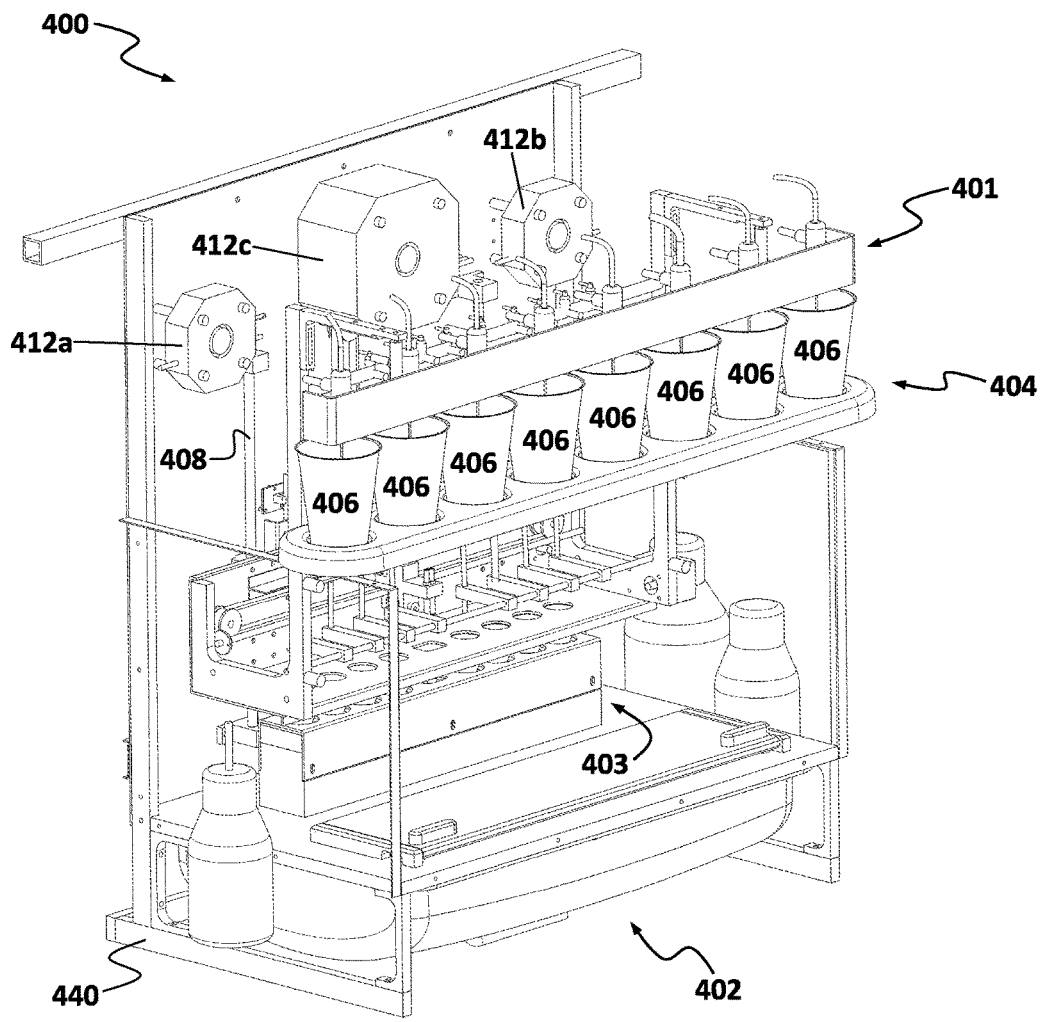
FIG. 4B illustrates a perspective view of the example automatic SPE apparatus of FIG. 4A, in a loading position, according to one or more aspects of the present application.

FIG. 4A shows a perspective view of one example automatic SPE apparatus 400 configured to provide an example implementation of the FIG. 3 automatic SPE system 300 in a pre-loading position. FIG. 4B shows a perspective view of the same example automatic SPE apparatus 400, but in a loading position.

Referring to FIGS. 4A and 4B, the automatic SPE apparatus 400 can include, a liquid loading assembly 401, a liquid drawing assembly 402, a cartridge housing tray 403 that can house a plurality of SPE cartridges 405, and a sample tray 404 holding a plurality of sample containers 406. Referring to FIGS. 4A, 4B, and 4G, the liquid loading assembly 401 can include a linear actuating mechanism, such as the example visible in FIG. 4G, comprising a belt-and-pulley mechanism 409, its driving motor (obstructed from view) and two guide bars 408, to effectuate vertical movement of the liquid loading assembly 401 along a linear vertical axis 407 from a pre-loading position as shown in FIG. 4A to a loading position as shown in FIG. 4B.

Figure 4C:
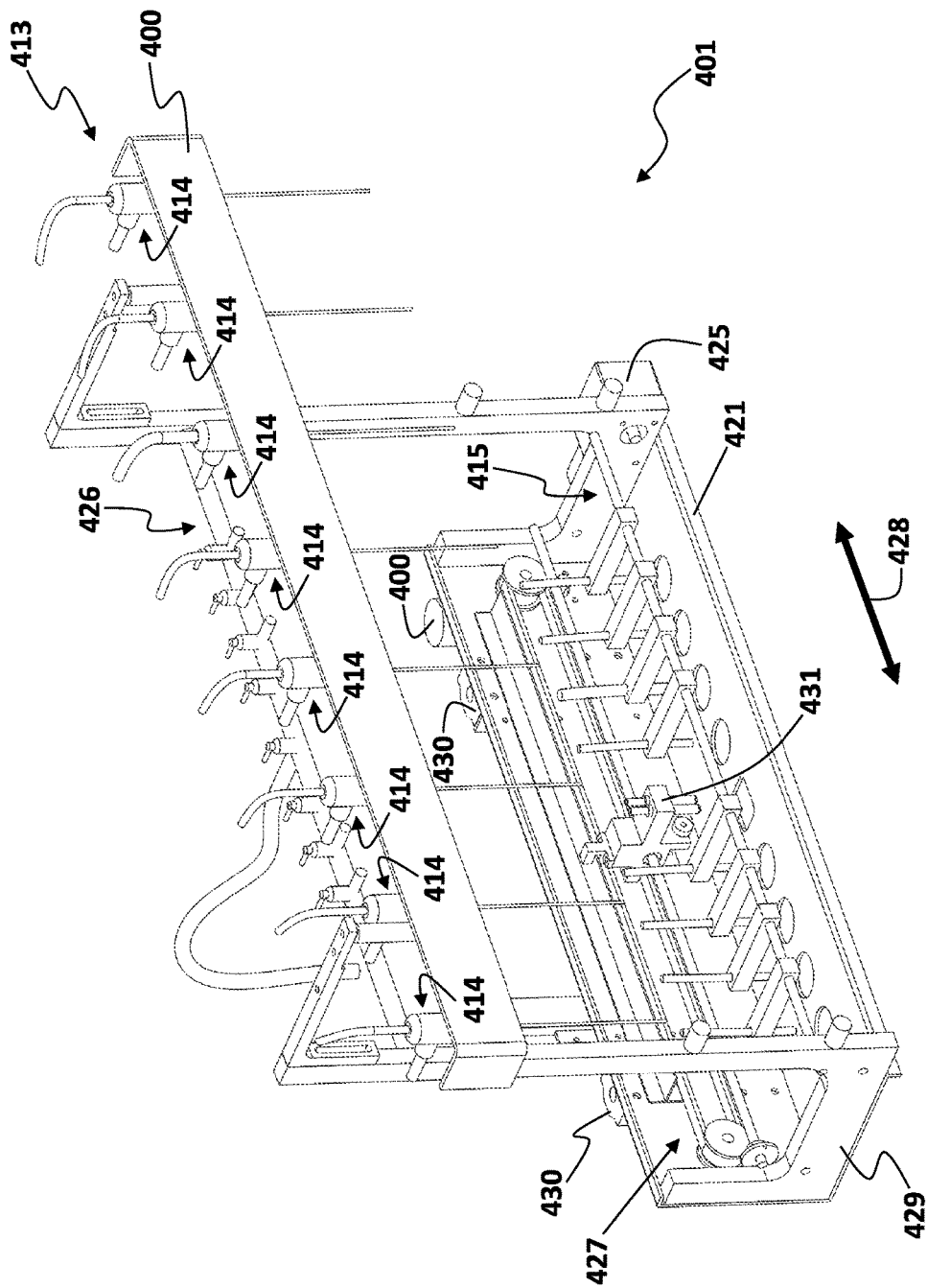
FIGS. 4C and 4D illustrate perspective views of an example liquid loading assembly, according to one or more aspects of the present application.
Figure 4D:
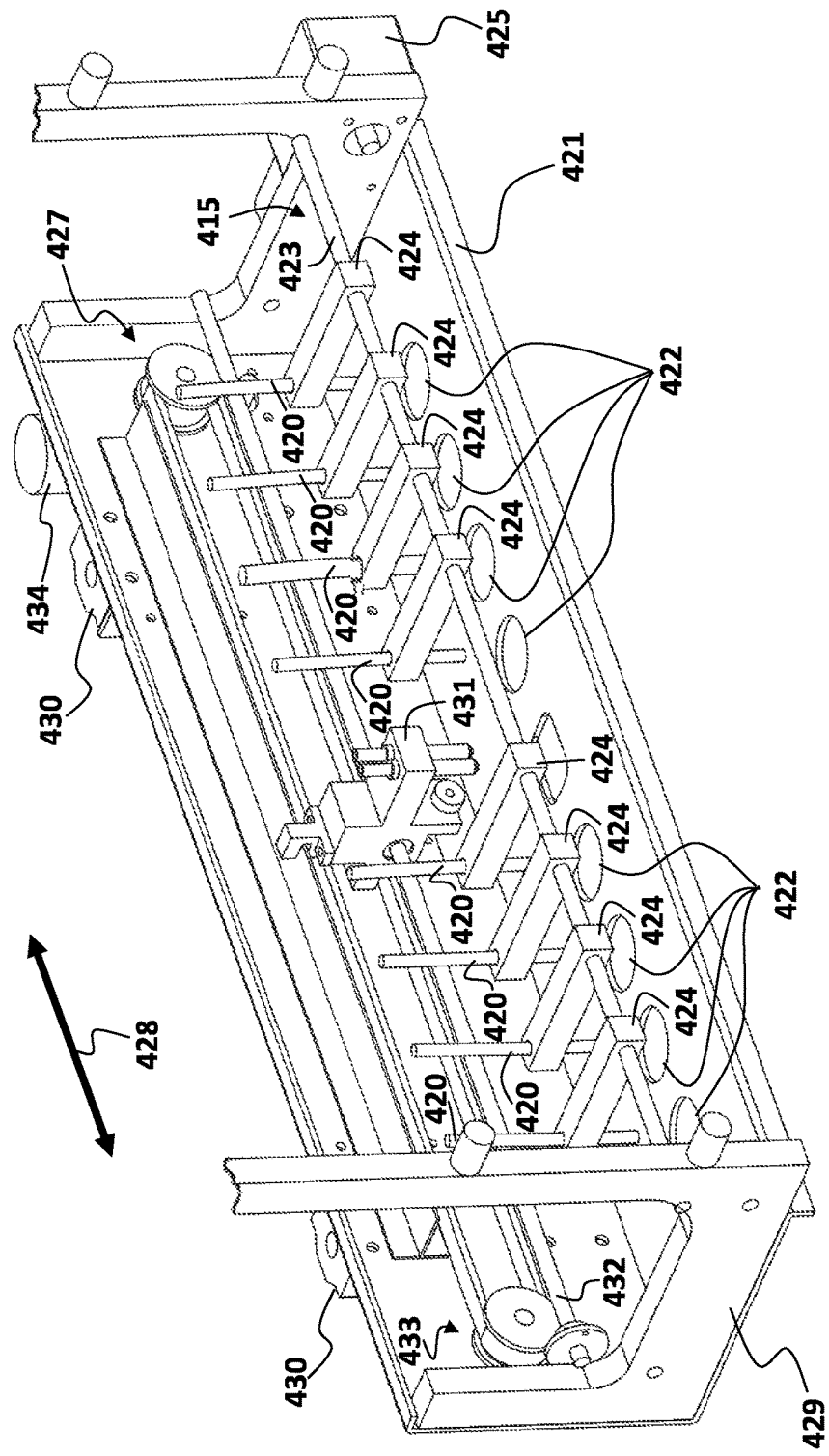

Referring to FIG. 4C, the liquid loading assembly 401 can include: a probe array 413 that can include a plurality of probe assemblies 414; a water distribution system 426 configured to distribute washing water between the probe assemblies 414; a tube holding assembly 415; a SPE solution loading mechanism 427; and a sealing member 421 having a plurality of holes 422.

According to an implementation, the probe array 413, the water distribution system 426, the tube holding assembly 415, the SPE solution loading mechanism 427, and the sealing member 421 can be mounted on a movable frame 429. The movable frame 429 can include two guiding members 430 configured to surround and, when urged by the linear actuating mechanism described above, to slide along guide bars 408, for linear movement along the vertical axis 407.

Figure 4E:
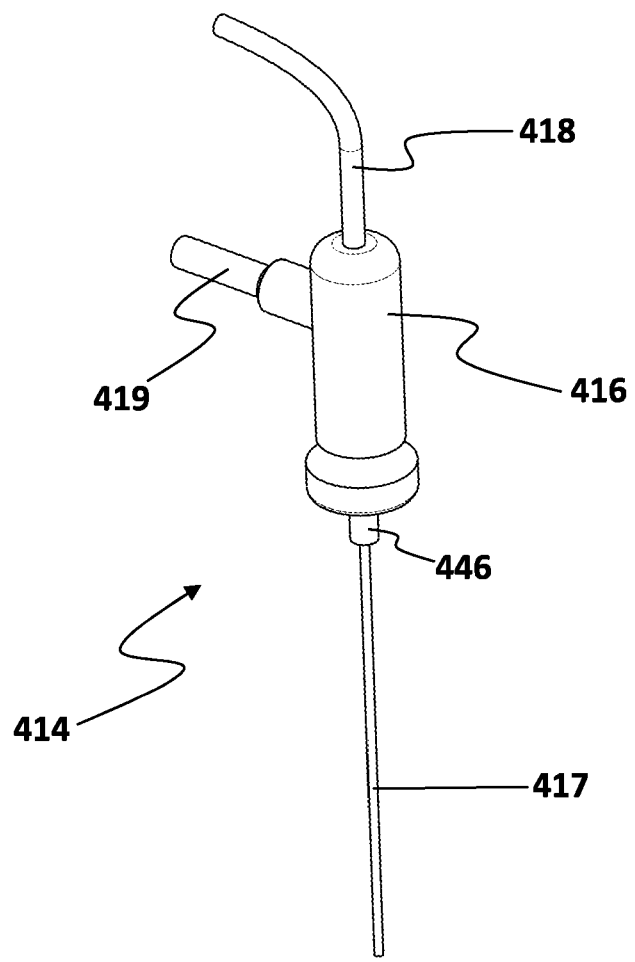
FIG. 4E illustrates an example probe assembly, according to one or more aspects of the present application.

FIG. 4E illustrates one example probe assembly 414 that can include a main body 416, a suction probe 417, a sample outlet 418, a water inlet 419, and a water outlet 446. Once the liquid loading assembly 401 is in the loading position (as shown in FIG. 4B), each suction probe 417 goes into a sample container 406 (visible and labeled in FIGS. 4A and 4B) that is placed underneath the suction probe 417. The sample can be pumped out of each sample container 406 via the suction probe 417 through the sample outlet 418 of each probe assembly 414.

Once the liquid loading assembly 401 is in its loading position (shown in FIG. 4B) the plurality of holes 422 on the sealing plate 421 can be placed tightly above the plurality of the SPE cartridges 405 (visible and labeled in FIG. 4A) to provide an air tight seal around the upper inlet 202 (labeled in FIG. 2) of the SPE cartridge 405.

Referring to FIG. 4D, the tube holding assembly 415 can include a motor 425, a shaft 423, and a plurality of tube holders 424 mounted on the shaft 423. The motor 425 and the shaft 423 can be configured to drive a roll rotation of the tube holders 424 in a rotational range of 90° about the longitudinal axis of the shaft, from a horizontal loading position (as shown in FIG. 4C) to a vertical idle position. The tube holders 424 can be configured to hold the plurality of injecting lines 420.

Referring to FIGS. 4A-4C, the sample outlet 418 (labeled in FIG. 4E) of each probe assembly 414 can be connected to a pump 412c via, for example a tube, and the pump 412c can be connected to an injecting line 420 (labeled in FIG. 4D) of a tube holder 424 (labeled in FIG. 4D) of the tube holding assembly 415. Once the tube holders 424 are in their horizontal injecting position, the pumped sample is introduced into the SPE cartridges 405 (labeled in FIG. 4A) via the injecting lines 420 (labeled in FIG. 4D) through the holes 422 (labeled in FIG. 4D) on the sealing plate 421 (labeled in FIGS. 4C and 4D) that can be placed tightly above the plurality of the SPE cartridges 405 (labeled in FIG. 4A).

Figure 4F:
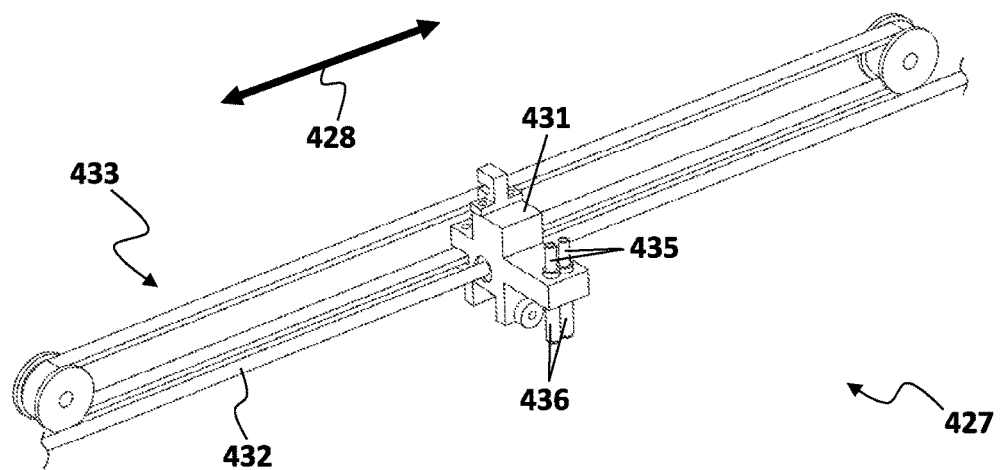
FIG. 4F illustrates an example SPE solution loading mechanism, according to one or more aspects of the present application.
Figure 4G:
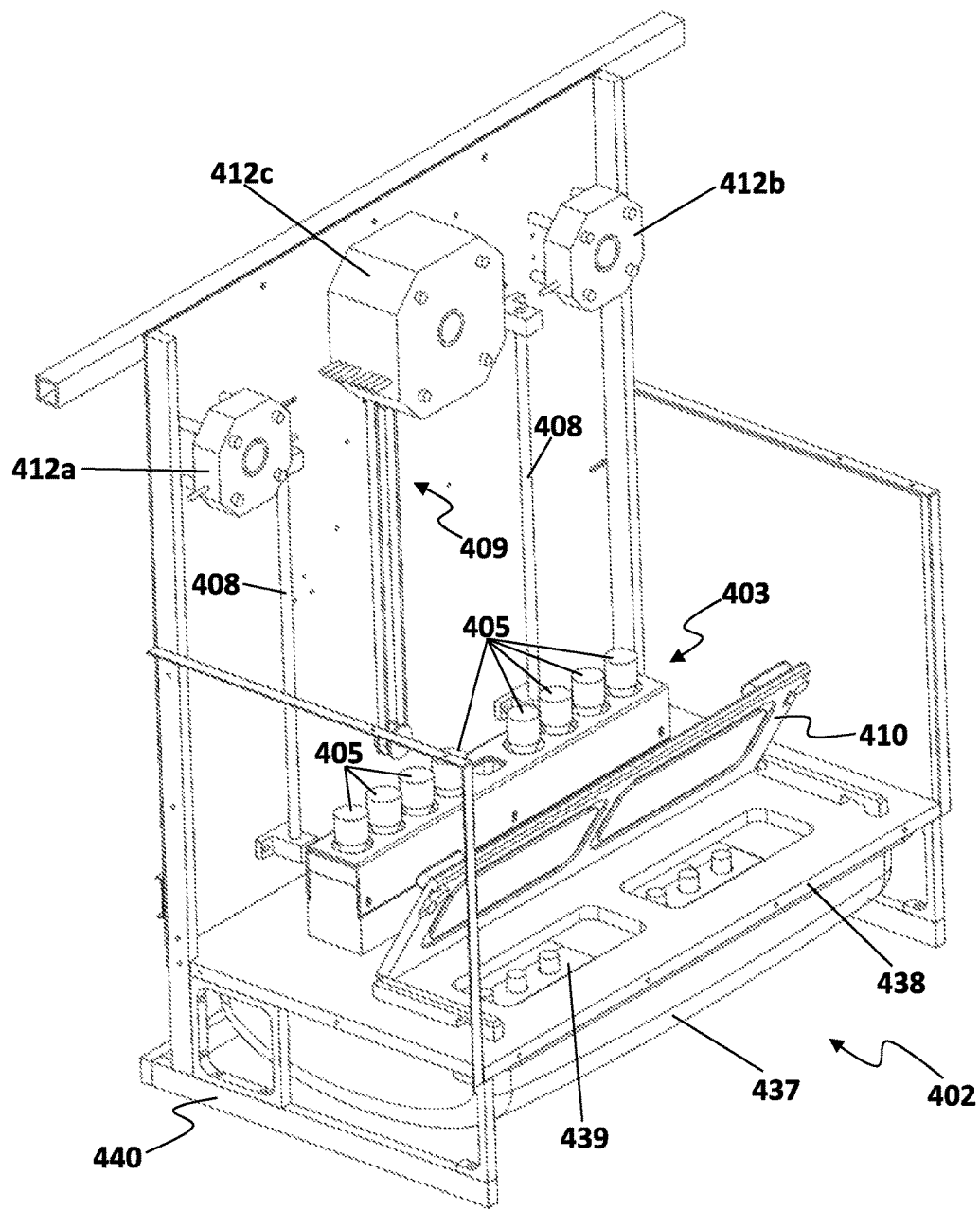
FIG. 4G illustrates a perspective view of one example automatic SPE apparatus without a liquid loading assembly, according to one or more aspects of the present application.

FIGS. 4C and 4F show an SPE solution loading mechanism 427 that can include a movable loading member 431. The movable loading member 431 can include two solution inlets 435 (visible and labeled in FIG. 4F) and two solution outlets 436 (visible and labeled in FIG. 4F). The movable loading member 431 can be in fluid connection with, for example two side pumps 412a and 412b (visible and labeled in FIGS. 4B and 4G) via solution inlets 435. The side pumps 412a and 412b can be configured to pump the activating solvent, washing solution, and the eluting solvent from SPE solution containers 411 to the loading member 431. The SPE solutions can be introduced into SPE cartridges 405 (labeled in FIG. 4A) via the two solution outlets 436. The movable loading member 431 is configured to be movable along a horizontal axis 428 that can be normal to the vertical axis 407. A motor 434 (shown in FIG. 4D) and a belt-and-pulley mechanism 433 can be utilized to drive the linear movement of the loading member 431 and a guide bar 432 can extend parallel to the axis 428, to provide a linear guide function of limiting the movement of the movable loading member 431 to a linear movement along the horizontal axis 428.

The movable loading member 431 can be configured to introduce the SPE solutions into SPE cartridges 405 one by one. An encoder can be used to determine the position of the movable loading member 431 along the guide bar 432. The movable loading member 431 can start the solution loading process at one end of the guide bar 432 over the first cartridge in the cartridge housing tray 403 (shown in FIGS. 4A and 4B), then it can move over the cartridges one by one using the feedback from the encoder, and end the solution loading process at the other end of the guide bar 432 over the last SPE cartridge in the cartridge housing tray 403. It will therefore be understood that the cartridge housing tray 403 can be configured to support the SPE cartridges 405 in a linear alignment that is parallel to the horizontal axis 428.

FIG. 4G illustrates the cartridge housing tray 403 and the liquid drawing assembly 402 mounted on the base frame 440 of the example automated SPE apparatus 400 (labeled in FIGS. 4A and 4B). As can be seen in this figure, the solution pumps 412a and 412b and the sample pump 412c along with the belt-and-pulley mechanism 409 and the guide bars 408 that provide the described vertical movement of the liquid loading assembly (not explicitly shown in FIG. 4G) can be mounted on the base frame 440.

Referring to FIG. 4G, the liquid drawing assembly 402 can include a vacuum chamber 437 and a top sealing member 438. The top sealing member 438 can include an access door 410 that can provide access to a plurality of eluate containers 441, as described later in greater detail. The cartridge housing tray 403 can be mounted on the top sealing member 438. The top sealing member 438 can have a plurality of holes under the cartridge housing tray 403 configured such that each hole is placed under a corresponding SPE cartridge 405, connecting the discharge of the SPE cartridges 405 to the vacuum chamber 437 and providing an air tight seal.

The vacuum chamber 437 can be connected to a vacuum pump (not explicitly shown in FIG. 4G). The vacuum pump can be utilized to create vacuum in the vacuum chamber 437, when necessary. The vacuum inside the vacuum chamber 437 can have two applications. First, since the discharge side of the SPE cartridges 405 can be connected to the vacuum chamber 437, once vacuum is provided inside the vacuum chamber 437 the solutions introduced into the SPE cartridges 405 can be forced to pass through the SPE cartridges 405 and be discharged inside the vacuum chamber 437. Second, the vacuum in the vacuum chamber 437 makes it possible to carry out evaporation and eluate concentration at lower temperatures, which will be discussed in more detail later in the present disclosure.

Figure 4H:
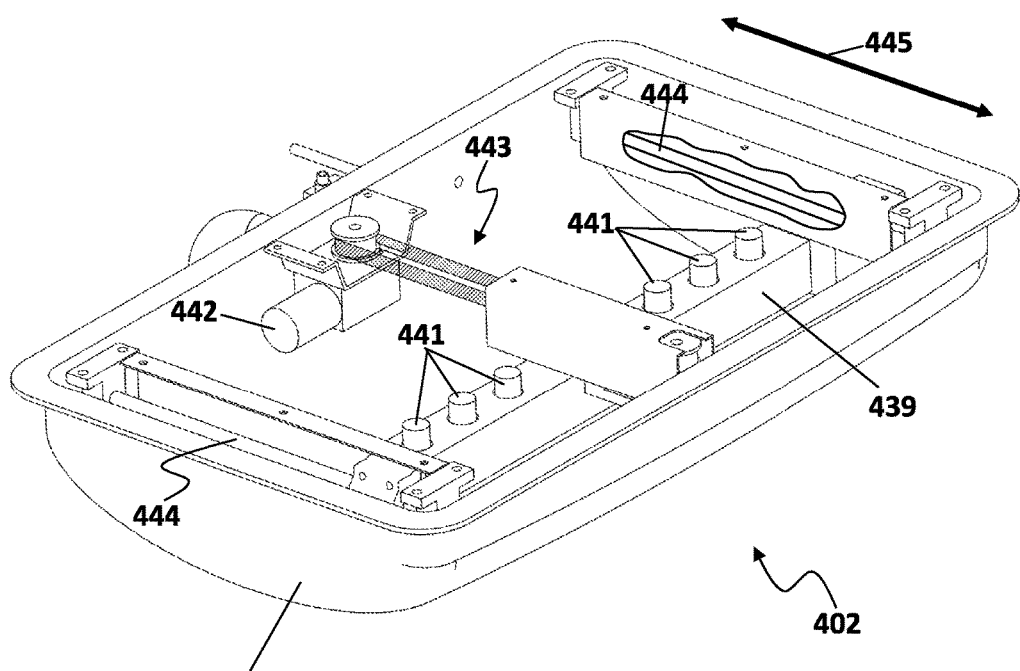
FIG. 4H illustrates an example liquid drawing assembly, according to one or more aspects of the present application.

FIG. 4H further illustrates various internal parts of the liquid drawing assembly 402. In this figure, the top sealing member 438 (shown in FIG. 4G) is not shown, so that the internal parts can be described in detail.

Referring to FIG. 4H, in one implementation, the eluate container movable support can include a movable tray 439, configured to hold the plurality of eluate containers 441 and movably coupled to guide bars 444, in a configuration that can guide movement of the movable tray 439 along a linear axis 445. The eluate container movable support can include a tray moving mechanism coupled to the movable tray 439, and configured to selectively urge the movement along the linear axis 445, to positions that can include an eluate loading position (which is visible in FIG. 4H) and a retrieval position. In the eluate loading position, each of the plurality of eluate containers 441 can be under the lower outlet of a respective one of the SPE cartridges. As will be described later in greater detail, when the movable tray 439 is in the eluate loading position, a vacuum can be formed in the vacuum chamber 437 to force the eluate solvent out of the SPE cartridges 405 and into the eluate containers 441. In one example implementation the tray moving mechanism can include a motor 442 and a belt-and-pulley mechanism 443. The motor 442 can have, for example, a rotating shaft (not explicitly visible in FIG. 4H) coupled to the movable tray 439 via the belt-and-pulley mechanism 443, which converts the shaft's rotation to linear movement of the movable tray 439 along the linear axis 445.

In an aspect, the vacuum chamber 437 can be provided with a drain hole (not visible in FIG. 4H), whereby the unwanted solutions can be discharged into special waste containers to avoid harming the environment with toxic residual solutions.

Referring to FIG. 4E, since the suction probe 417 is in contact with the sample, in order to wash the suction probe for the next runs, a washing mechanism can be utilized to automatically wash the probe assemblies 414, especially the suction probes 417. As shown in FIG. 4E, the suction probe 417 of each probe assembly 414 can be placed inside the water outlet 446, which can be configured as a sleeve around the suction probe 417. The water inlet 419 of each probe assembly 414 can be connected to the water distribution system 426 (visible and labeled in FIG. 4C). Water can be injected through the water inlet 419 and then discharged from the water outlet 446 to wash the outer surface of the suction probe 417.

Figure 4I:
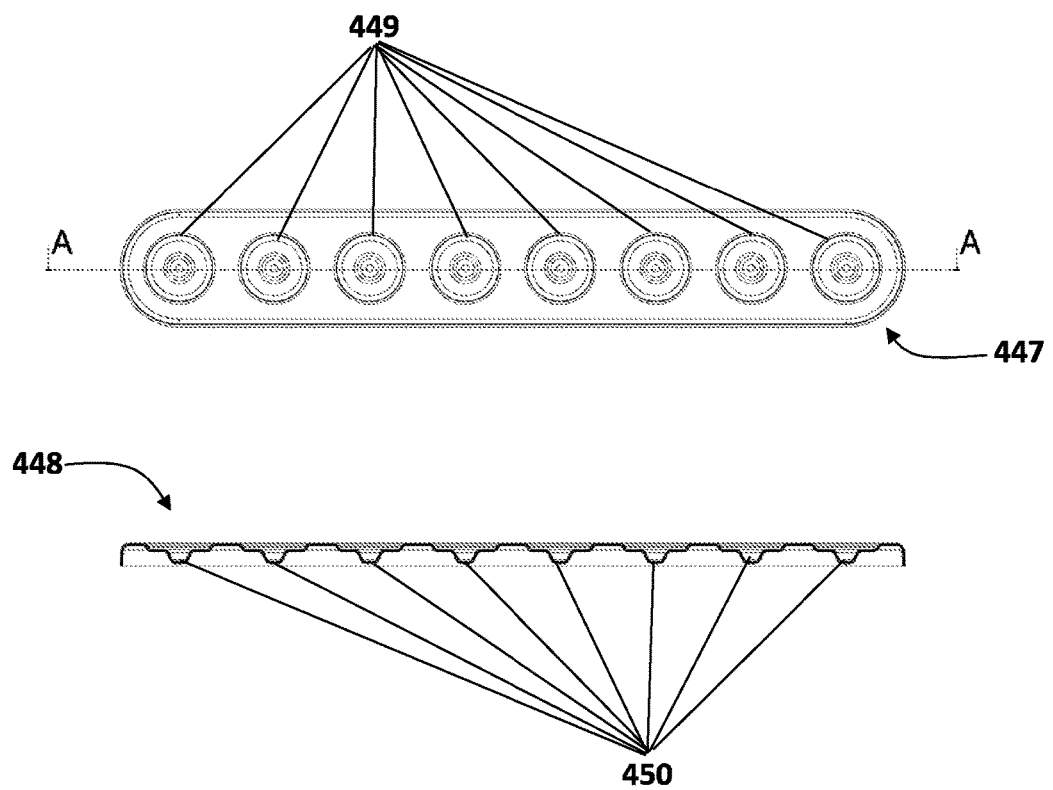
FIG. 4I illustrates top and sectional view of an example sample tray, according to aspects of the present disclosure.

FIG. 4I illustrates a top view 447 and a sectional view 448 of the sample tray 404. Referring to FIG. 4I, the sample tray 404 includes a plurality of housing holes 449 for housing the sample containers 406 (shown in FIGS. 4A and 4B). Inside each housing hole 449 there can be a smaller hole 450.

In one example operation, to prepare the system for carrying out the washing process, the sample containers 406 can be removed from the sample tray 404. The tip of the suction probes 417 can be lowered inside these smaller holes 450. Once the water is injected into the probe assembly 414 it is discharged from the water outlet 446. Since the suction probe 417 is placed inside the water outlet 446, the discharged water washes the outer surface of the suction probes 417. Meanwhile the discharged water can be drawn inside the suction probe 417 using the sample pump 412c in order to wash the inner surface of the suction probe 417. During the washing process, the SPE cartridges 405 can be removed from the cartridge housing tray 403 and the washing water can be discharged into the vacuum chamber 437, from which it can be discharged into a waste container.

Figure 5A:
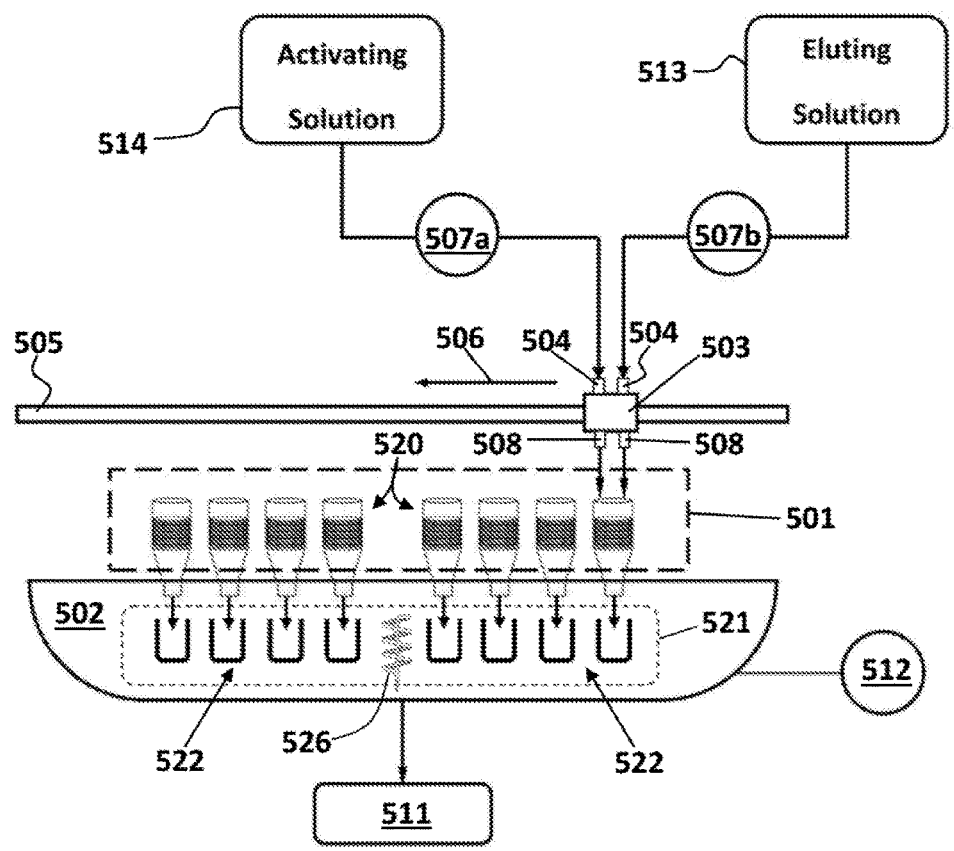
FIGS. 5A and 5B illustrate flow diagrams of an example automatic SPE apparatus pursuant to aspects of the present disclosure.
Figure 5B:
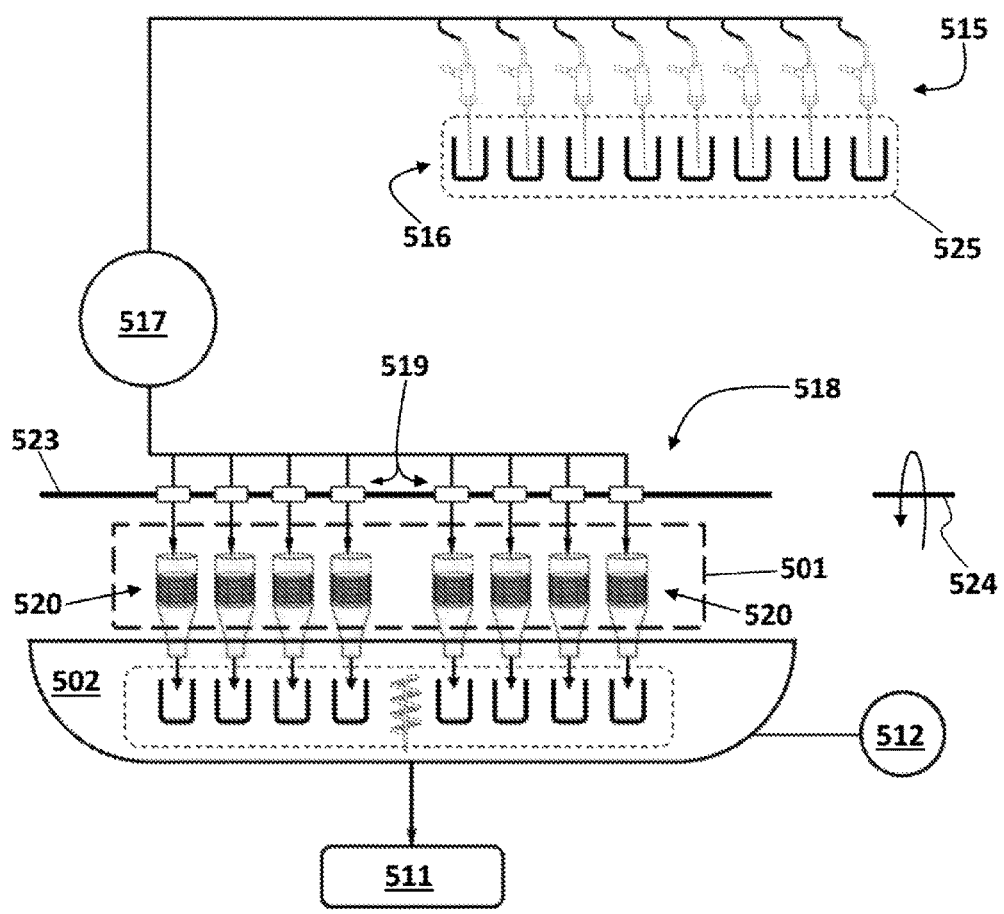

FIGS. 5A and 5B illustrate a simplified flow diagram of FIGS. 4A and 4B automated SPE apparatus 400. Referring to FIGS. 5A and 5B, automatic implementation of FIG. 1 SPE method 100 utilizing the exemplar automated SPE apparatus 400 can be described in the following sections of the present disclosure in connection with FIG. 1 SPE method 100.

Example 1: Activating the Solid Bed (i.e., Activating Step)

Referring to FIG. 5A, according to an implementation, a pump 507a, for example a peristaltic pump, can be utilized to introduce the activating solvent or buffer into a plurality of SPE cartridges 520 housed in a cartridge housing tray 501. The pump 507a can be connected to an activating solvent container 514 from its suction side and to a solution inlet 504 of a movable loading member 503 from its discharge side. The movable loading member 503 can be configured to distribute the activating solvent into the plurality of SPE cartridges 520. The movable loading member 503 can be configured to start distributing the activating solvent from a starting position (as shown in FIG. 5A) on top of the first SPE cartridge 509, then move along a longitudinal axis 506 of a guide bar 505 on top of each SPE cartridge 520 to an end position (not shown in FIG. 5A) on top of the last cartridge 510. A specific amount of the activating solvent can be introduced by the movable loading member 503 into each SPE cartridge 520. The position of the movable loading 503 member on top of each cartridge 520 can be encoded by, for example, an optical encoder that can be coupled to the movable loading member 503. Once the activating solvent is distributed in all SPE cartridges 520, a delay may be employed for the activating solvent to wet the solid bed inside the SPE cartridge 520. A vacuum pump 512 connected to a vacuum chamber 502 can then be utilized to provide vacuum under the plurality of SPE cartridges 520 to force the activating solvent out of the SPE cartridges 520. The vacuum chamber 502 can include an eluate movable tray 521 that can be configured to house a plurality of eluate containers 522, and that can be movable along a horizontal axis between a loading position and a retrieval position, such as described in reference to FIGS. 4G and 4H. During the activation step, the eluate movable tray 521 is in its retrieval position (as shown in FIG. 4H) and the eluate containers 522 are not positioned under the discharge of the plurality of SPE cartridges 520, therefore, the residual activating solvent can be discharged into a waste container 511 via a drain (not explicitly visible in FIG. 5A) under the vacuum chamber 502.

Example 2: Loading the Sample (i.e., Sample Loading Step)

Referring to FIG. 5B, according to an implementation, a sample pump 517, for example a peristaltic pump, can be utilized to introduce the sample solution into the plurality of SPE cartridges 520 housed in the cartridge housing tray 501. The sample pump 517 can be connected to a plurality of probe assemblies 515 from its suction side and to a plurality of tube holders 519 of a tube holding mechanism 518 from its discharge side. The plurality of probe assemblies 515 can be configured for drawing the sample solution from a plurality of sample containers 516 housed in a sample tray 525 and the plurality of the tube holders 519 can be configured to introduce the sample solution into the plurality of SPE cartridges 520. Once the sample solution is introduced into all the SPE cartridges 520, the vacuum pump 512 connected to the vacuum chamber 502 can be utilized to provide vacuum under the plurality of the SPE cartridges 520 to force the sample solution downward inside the SPE cartridges 520 in order to ensure an optimal retention of the sample solution and to force air pass through the cartridges 520 in order to dry the water accompanying the sample. The tube holding mechanism 518 can further include a shaft 523 that can be coupled to a motor (not explicitly visible in FIG. 5B). The motor (not explicitly visible in FIG. 5B) can be configured to drive a roll-rotation of the shaft 523 about an axis 524 in a rotation range of 90° from a substantially vertical idle position to a substantially horizontal loading position (as shown in FIGS. 4B-4D).

Example 3: Washing the Loaded Sample (i.e., Washing Step)

Referring to FIG. 5A, according to an implementation, a pump 507a, for example, a peristaltic pump, can be utilized to introduce the washing solution or buffer into the plurality of SPE cartridges 520 housed in the cartridge housing tray 501. The pump 507a can be connected to a washing solution container (not shown in FIG. 5A) from its suction side and to the solution inlet 504 of the movable loading member 503 from its discharge side. The movable loading member 503 can be configured to distribute the washing solution into the plurality of SPE cartridges 520. The movable loading member 503 can be configured to start distributing the washing solution from a starting position (as shown in FIG. 5A) on top of the first SPE cartridge 509, then move along a longitudinal axis 506 of a guide bar 505 on top of each SPE cartridge 520 to an end position (not shown in FIG. 5A) on top of the last cartridge 510. A specific amount of the washing solution can be introduced by the movable loading member 503 into each SPE cartridge 520. The position of the movable loading 503 member on top of each cartridge 520 can be encoded by, for example an optical encoder that can be coupled to the movable loading member 503. Once the washing solution is distributed in all SPE cartridges 520, a vacuum pump 512 connected to a vacuum chamber 502 can be utilized to provide vacuum under the plurality of SPE cartridges 520 to force the washing solution containing the interferences out of the SPE cartridges 520. During the washing step, the eluate movable tray 521 is in its retrieval position (as shown in FIG. 4H) and the eluate containers 522 are not positioned under the discharge of the plurality of SPE cartridges 520, therefore, the residual washing solution can be discharged into a waste container 511 via a drain (not explicitly visible in FIG. 5A) under the vacuum chamber 502.

Example 4: Eluting the Compound of Interest (i.e., Eluting Step)

Referring to FIG. 5A, according to an implementation, at the beginning of eluting step, the eluate movable tray 521 that is configured to house a plurality of the eluate containers 522 can be moved from its retrieval position (as shown in FIG. 4H) to its loading position under the discharge of the plurality of the SPE cartridges 520 and the eluate containers 522 can be positioned under the discharge of the plurality of SPE cartridges 520. According to an implementation, a pump 507b, for example, a peristaltic pump, can be utilized to introduce the eluting solvent (i.e., eluent) into the plurality of SPE cartridges 520 housed in the cartridge housing tray 501. The pump 507b can be connected to an eluting solvent container 513 from its suction side and to the solution inlet 504 of the movable loading member 503 from its discharge side. The movable loading member 503 can be configured to distribute the eluting solvent into the plurality of SPE cartridges 520. The movable loading member 503 can be configured to start distributing the eluting solvent from a starting position (as shown in FIG. 5A) on top of the first SPE cartridge 509, then move along a longitudinal axis 506 of a guide bar 505 on top of each SPE cartridge 520 to an end position (not shown in FIG. 5A) on top of the last cartridge 510. A specific amount of the eluting solvent can be introduced by the movable loading member 503 into each SPE cartridge 520. The position of the movable loading 503 member on top of each cartridge 520 can be encoded by, for example an optical encoder that can be coupled to the movable loading member 503. Once the eluting solvent is distributed in all the SPE cartridges 520, the vacuum pump 512 connected to the vacuum chamber 502 can be utilized to provide vacuum under the plurality of the SPE cartridges 520 to force the eluting solvent out of the SPE cartridges 520 to obtain an eluate solution containing the compound of interest. The eluate can be discharged into the plurality of eluate containers 522.

Example 5: Concentrating the Compound of Interest in the Eluate (i.e., Concentrating Step)

The discharged eluate solution inside the eluate containers 522 can be concentrated by a controlled evaporation of the eluting solvent inside the eluate solution. As used herein, a "controlled evaporation" means an "evaporation at lower temperatures" in order to avoid the evaporation of volatile components along with the eluting solvent. In the concentrating step, vacuum is provided inside the vacuum chamber 502 using the vacuum pump 512. The vacuum reduces the evaporation temperature and may make it possible to evaporate the eluting solvent from the eluate solution at lower temperatures and obtain a concentrated compound of interest in the eluate containers 522. In an implementation, a heater 526 can be utilized to heat the eluate containers 522. Once the concentrated compound of interest is obtained, the eluate movable tray 521 containing the eluate containers 522 can be moved back to its retrieval position under the access door (labeled 410 in FIG. 4G) of the vacuum chamber 502 in order for a technician to retrieve the eluate containers 522 containing the compounds of interest, which later can be subjected to various detection methods.

It may become apparent to a person skilled in the art, upon reading this disclosure, that the automated SPE apparatus according to different aspects of the present disclosure can be configured to automatically implement different SPE methods, including, but not limited to reversed-phase SPE method with different aqueous samples including biological fluids (serum, plasma, urine), aqueous extracts of tissues, and environmental water samples. The common applications could be extracting drugs and metabolites in biological fluids, extracting environmental pollutants in water and obtaining aqueous extracts of tissues and solids.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. An apparatus for solid phase extraction (SPE), the apparatus comprising:
   a cartridge housing tray configured to house a plurality of SPE cartridges, each of the plurality of SPE cartridges having an inlet and an outlet;
   a liquid loading assembly configured to:
      introduce a respective amount of an activating solvent into the inlet of each of the plurality of SPE cartridges,
      transfer into the respective inlets of the plurality of SPE cartridges a corresponding plurality of samples,
      introduce a respective amount of a washing solution into the inlet of each of the plurality of SPE cartridges, and
      introduce a respective amount of an eluting solvent to the inlet of each of the plurality of SPE cartridges; and
   a liquid drawing assembly configured to
      selectively apply a drawing driving force to the outlets of the plurality of SPE cartridges to draw out of all the SPE cartridges, from their respective outlets and into a pan, the respective activating solvent and washing solution introduced into the inlets by the liquid loading assembly, and to draw the eluting solvent out of all the plurality of SPE cartridges, through their respective outlets, and to collect the drawn eluting solvent in a corresponding plurality of eluate containers, and
      evaporate the eluting solvent from the plurality of eluate containers;
   wherein the inlet is an upper inlet, at an upper end of the SPE cartridge, and the outlet is a lower outlet, at a lower end of the SPE cartridge, and wherein the liquid drawing assembly comprises:
   a vacuum chamber connected to the lower outlets of the plurality of the SPE cartridges; and
   an eluate container movable support, configured to support and move the plurality of the eluate containers, along a horizontal axis, to positions including an eluate loading position and a position away from the eluate loading position,
   wherein the vacuum chamber is configured to apply a vacuum at the lower outlet of the plurality of the SPE cartridges as the drawing driving force, and
   wherein, in the eluate loading position, each of the plurality of eluate containers is under the lower outlet of a respective one of the SPE cartridges, to collect the respective eluate drawn from the lower outlet;
   further comprising a sample tray, configured to hold a plurality of sample containers, wherein the liquid loading assembly comprises:
   a frame guide, extending along a vertical axis, the vertical axis being normal to the horizontal axis;

a movable frame, movably coupled to the frame guide, in a configuration constraining the movable frame to a vertical movement, parallel to the vertical axis, between positions that include a loading position and a preloading position;

a linear actuating mechanism, coupled to the movable frame and configured to selectively urge the vertical movement;

a plurality of probe assemblies, supported by the movable frame, each of the probe assemblies corresponding to one of the sample containers, and each of the probe assemblies including a suction probe and a sample outlet;

a sample pump, connected to the plurality of sample outlets by a corresponding plurality of tubes; and a plurality of injector lines, each connected at one end to an output of the sample pump and each having a distal end, wherein the plurality of probe assemblies and the movable frame are configured such that, in the loading position, the suction probe goes into the corresponding sample container, and wherein in the loading position, the sample pump draws a respective content of each of the sample containers through a corresponding one of the tubes, and injects the content through a corresponding one of the injector lines into the upper inlet of a corresponding one of the SPE cartridges.

2. The apparatus of claim 1, wherein the vacuum chamber is further configured to apply a vacuum at the lower outlet of the plurality of the SPE cartridges to force the samples transferred into the respective inlets of the plurality of SPE cartridges downward inside the SPE cartridges.

3. The apparatus of claim 1, wherein the eluate container movable support comprises tray guide bars, extending along the horizontal axis, a movable eluate container tray that is movably coupled to the tray guide bars, and a tray moving mechanism coupled to the movable eluate container tray, wherein the movable eluate container tray is movably coupled to the tray guide bars in a configuration wherein the movable eluate container tray is constrained by the tray guide bars to movement along the horizontal axis.

4. The apparatus of claim 1, wherein the movable eluate container tray further comprises a heating mechanism configured to evaporate, within the vacuum of the vacuum chamber, the eluting solvent from the eluate in the eluate containers.

5. The apparatus according to claim 1, wherein the liquid loading assembly further comprises:
a shaft, extending along a longitudinal axis, supported to be rotatable about the longitudinal axis;
a plurality of tube holders, each mounted on the shaft, each supporting the distal end of a corresponding one of the injector lines; and
a motor, coupled to the shaft, wherein a rotation of the motor drives a roll rotation of the shaft about the longitudinal axis, between a horizontal loading position and a vertical idle position,
wherein, in the horizontal loading position, while the movable frame is in the loading position, the distal end of each the plurality of injector lines is proximal to the upper inlet of a corresponding one of the SPE cartridges.

6. The apparatus according to claim 5, wherein the cartridge housing tray is configured to house the plurality of SPE cartridges in an arrangement wherein the respective upper inlets are aligned linearly along an alignment axis that extends perpendicular to the horizontal axis and normal to the vertical axis, wherein the apparatus further comprises
a movable loading member, selectively movable in a direction parallel to the alignment axis, to respective positions, each of the positions being above the upper inlet of a corresponding one of the SPE cartridges and, at each of the positions, to selectively introduce the respective amount of activating solvent through the upper inlet into the SPE cartridge.

7. The apparatus according to claim 6, wherein the movable loading member includes a solution inlet and a solution outlet, wherein the apparatus further comprises a side pump, the side pump being configured to selectively pump the respective amount of activating solvent from an activating solvent container, into the solution inlet, and out from the solution outlet into the inlet of the SPE cartridge.

8. The apparatus according to claim 7, wherein the side pump is configured to selectively pump the respective amount of washing solution, from a washing solution container, into the solution inlet, and out from the solution outlet into the inlet of the SPE cartridge.

9. The apparatus according to claim 8, wherein the side pump is configured to selectively pump the respective amount eluate solvent, from an eluate solvent container, into the solution inlet, and out from the solution outlet into the inlet of the SPE cartridge.

* * * * *